(12) United States Patent
Brumleve et al.

(10) Patent No.: US 8,241,230 B2
(45) Date of Patent: Aug. 14, 2012

(54) VARIABLE STIFFNESS WIRE GUIDE

(75) Inventors: John A Brumleve, Bloomington, IN (US); Brian L Bates, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 255 days.

(21) Appl. No.: 11/860,837

(22) Filed: Sep. 25, 2007

(65) Prior Publication Data

US 2009/0082851 A1    Mar. 26, 2009

(51) Int. Cl.
*A61B 5/00* (2006.01)
*A61M 25/00* (2006.01)

(52) U.S. Cl. ........................................................ 600/585

(58) Field of Classification Search .................. 600/585, 600/433, 434, 462; 604/524, 523, 526
See application file for complete search history.

(56) References Cited

U.S. PATENT DOCUMENTS

| | | | |
|---|---|---|---|
| 3,452,742 A | 7/1969 | Muller | |
| 3,547,103 A | 12/1970 | Cook | |
| 3,789,841 A | 2/1974 | Antoshkiw | |
| 4,003,369 A | 1/1977 | Heilman et al. | |
| 4,215,703 A | 8/1980 | Wilson | |
| 4,824,435 A | 4/1989 | Giesy et al. | |
| 4,971,490 A | 11/1990 | Hawkins | |
| 5,354,257 A | 10/1994 | Roubin et al. | |
| 5,957,903 A * | 9/1999 | Mirzaee et al. | 604/524 |
| 6,113,557 A * | 9/2000 | Fagan et al. | 600/585 |
| 6,183,420 B1 * | 2/2001 | Douk et al. | 600/462 |
| 6,254,550 B1 | 7/2001 | McNamara et al. | |
| 2004/0210163 A1 | 10/2004 | Osawa et al. | |
| 2005/0054953 A1 | 3/2005 | Ryan et al. | |

FOREIGN PATENT DOCUMENTS

| | | |
|---|---|---|
| JP | 01124473 | 5/1989 |
| WO | WO84/04686 | 12/1984 |

* cited by examiner

*Primary Examiner* — Brian Szmal
(74) *Attorney, Agent, or Firm* — Brinks Hofer Gilson & Lione

(57) ABSTRACT

The present invention provides a wire guide having a variable stiffness region that may be selectively adjusted to vary the stiffness along a portion of the wire guide. The wire guide generally comprises an outer core member and an inner core member, wherein the inner core member is disposed for longitudinal movement with respect to the outer core member. The outer core member is attached to a proximal end of a coiled member, while the inner core member is attached to the coiled member at an attachment region between proximal and distal ends of the coiled member. In operation, distal advancement of the outer core member with respect to the inner core member causes the coiled member to compress at a location between the proximal end of the coiled member and the attachment region, thereby selectively increasing the stiffness along a portion of the length of the wire guide.

25 Claims, 3 Drawing Sheets

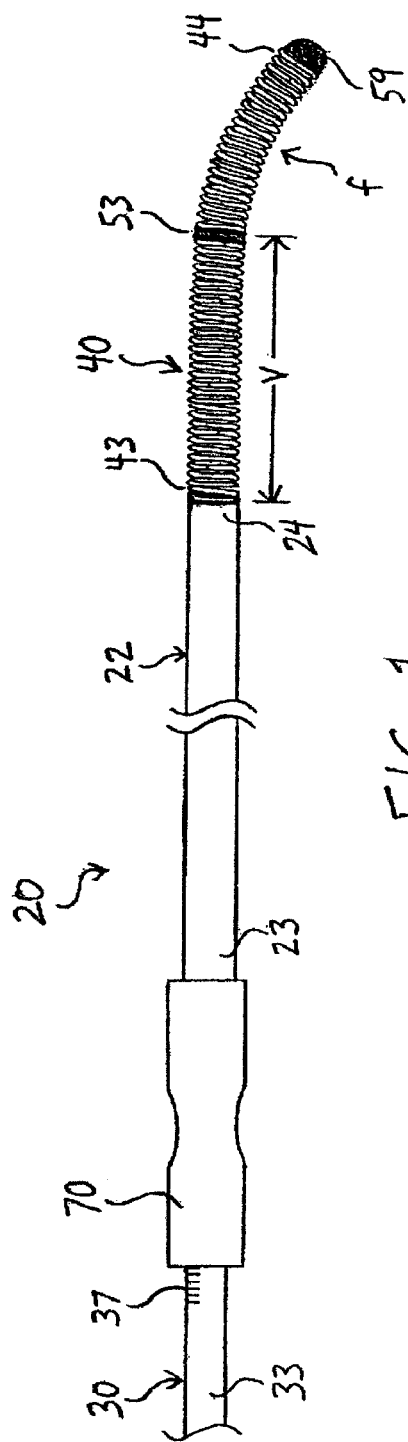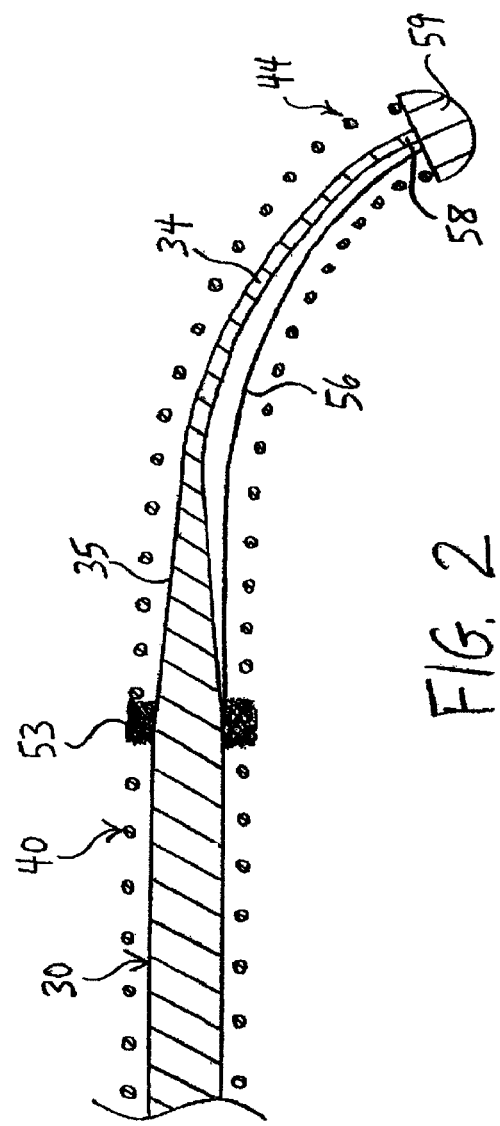

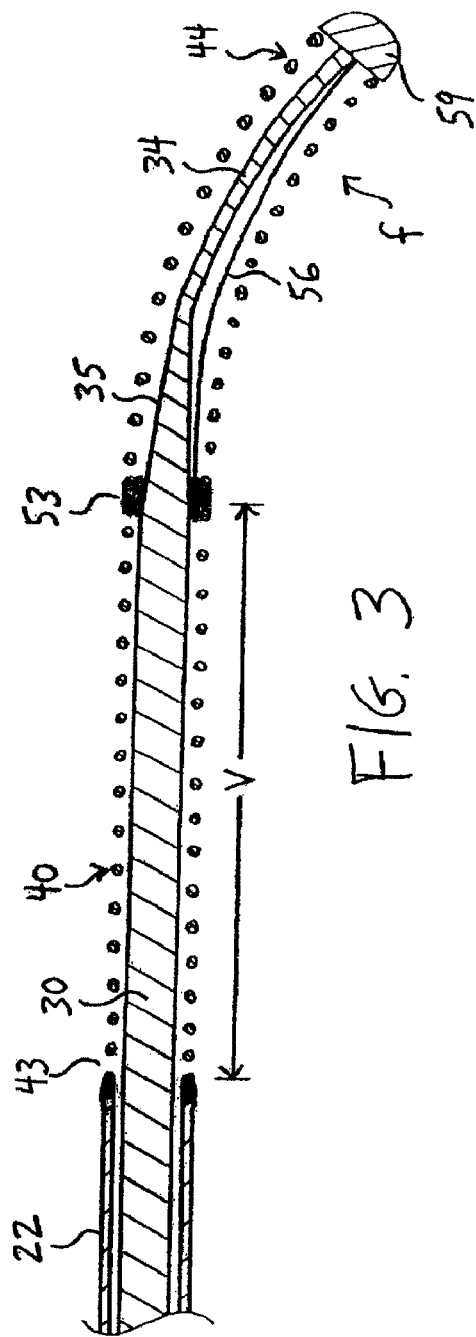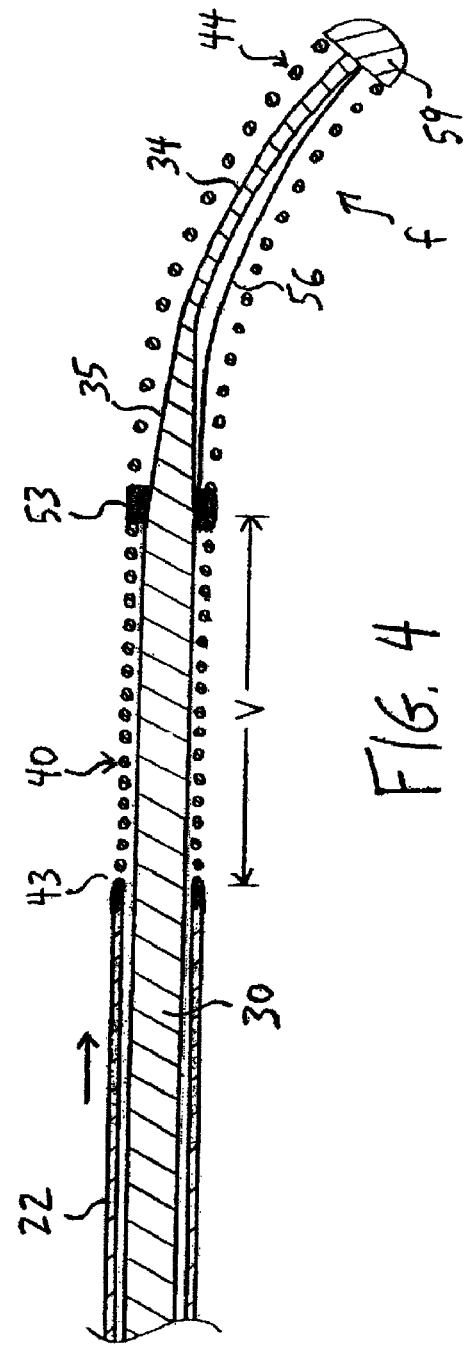

VARIABLE STIFFNESS WIRE GUIDE

BACKGROUND

The present invention relates generally to apparatus and methods for treating vascular conditions, and more specifically, to a wire guide having at least one variable stiffness region, and a method for varying the stiffness of at least a portion of the wire guide.

Wire guides are commonly used in vascular procedures, such as angioplasty procedures, diagnostic and interventional procedures, percutaneous access procedures, and radiological and neurological procedures. In general, wire guides may be used to introduce a wide variety of medical devices into the vascular system.

For example, wire guides may be employed to treat atherosclerosis and other occlusive diseases, which are prevalent among a significant portion of the population. In such diseases, atherosclerotic plaque forms on the walls of the vessel and blocks or restricts blood flow through the vessel. Atherosclerosis commonly affects the coronary arteries, the aorta, the iliofemoral arteries and the carotid arteries. Several serious conditions may result from the restricted blood flow, such as ischemic events.

Various procedures are known for treating stenoses in the arterial vasculature, such as the use of balloon angioplasty and stenting. During a balloon angioplasty procedure, a catheter having a deflated balloon attached thereto is positioned across a constricting lesion, and the balloon is then inflated to widen the lumen to partially or fully restore patency to the vessel.

Stenting involves the insertion of a usually tubular member into a vessel, and may be used alone or in conjunction with an angioplasty procedure. Stents may be self-expanding or balloon expandable. Self-expanding stents typically are delivered into a vessel within a delivery sheath, which constrains the stent prior to deployment. When the delivery sheath is retracted, the stent is allowed to radially expand to its predetermined shape. If the stent is balloon expandable, the stent typically is loaded onto a balloon of a catheter, inserted into a vessel, and the balloon is inflated to radially expand the stent.

Stents also may also be used in conjunction with a stent-graft procedure, wherein the stent may be coupled to an inner or outer surface of a graft material, or disposed between layers of graft material. In stent-graft procedures, it may be desirable to place one or more stent-graft limbs in position within a main body stent-graft. In other instances, such as branch vessel stent grafting, it may be desirable to place a limb within a limb.

Generally, during each of the foregoing procedures, a wire guide is first inserted into a patient's vessel, e.g., under fluoroscopic guidance. The wire guide then is advanced toward a target site in the patient's vasculature. For example, the distal end of the wire guide may be advanced through a stenosis. Then, various medical components, such as a balloon catheter and/or stent, may be distally advanced over the wire guide to the target site.

Various wire guides comprise flexible distal regions to facilitate navigation through the tortuous anatomy of a patient's vasculature. Where such flexible distal regions are used, it may be difficult to insert a medical component over the wire guide, for example, because the flexible distal region may be susceptible to kinking. However, if the distal region of the wire guide is too rigid, then it may not be sufficiently flexible to navigate the tortuous anatomy.

Therefore, in order to facilitate advancement of medical components to the target site, some medical procedures first use a relatively flexible wire guide to navigate the patient's anatomy. Then, a buddy wire, having a slightly greater rigidity than the initial wire guide, is inserted over the initial wire guide and the initial wire guide is subsequently removed. A medical component, such as a catheter, then may be advanced distally over the buddy wire so that instances of kinking may be reduced. However, this technique requires the insertion of two wires, i.e., the initial wire guide and the buddy wire, to enable positioning of the medical components at the target site, thereby increasing the time, cost and complexity of the procedure.

In view of the foregoing, there is a need for a single wire guide having a variable stiffness suitable for navigating tortuous anatomy, but also being sufficiently rigid to permit the advancement of medical components over the wire guide.

SUMMARY

The present invention provides a wire guide having a variable stiffness that may be selectively adjusted along a portion of the wire guide.

In a first embodiment, the wire guide comprises an outer core member, an inner core member, and a coiled member, each having proximal and distal ends. The outer core member is disposed over a proximal portion of the inner core member for longitudinal movement with respect to the inner core member. The distal end of the outer core member is attached to the proximal end of the coiled member, which is disposed over a distal portion of the inner core member. The inner core member is attached to the coiled member at an attachment region of the coiled member between the proximal and distal ends of the coiled member. The inner core member may extend beyond the attachment region to the distal end of the coiled member, and may be affixed to an atraumatic tip. A variable stiffness region is formed between the proximal end of the coiled member and the attachment region. A fixed stiffness region is formed between the attachment region and the atraumatic tip.

In operation, distal advancement of the outer core member with respect to the inner core member causes the coiled member to compress along the variable stiffness region. This causes an increase in the stiffness along the length of the variable stiffness region. However, the fixed stiffness region, which is disposed distal to the variable stiffness region, maintains its flexibility, which may be suitable for insertion into a patient's vessel and may be configured to navigate tortuous anatomy.

During insertion of the wire guide, the variable stiffness region may be provided in a relaxed state, whereby it also may be suitable for navigating tortuous anatomy. Thereafter, the stiffness of the variable stiffness region may be increased, for example, to facilitate advancement of medical components over a greater portion of the wire guide.

An activation mechanism may be provided for causing selective advancement of the outer core member in proximal and distal directions with respect to the inner core member. The activation mechanism may comprise a rotatable handle to permit selective adjustment in positioning between the inner and outer core members, thereby selectively varying the stiffness of the variable stiffness region of the wire guide.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead being placed upon illustrating the principles of the invention. Moreover, in the figures, like referenced numerals designate corresponding parts throughout the different views.

FIG. 1 is a side view of a variable stiffness wire guide provided in accordance with a first embodiment.

FIG. 2 is a side-sectional view of a distal region of the wire guide of FIG. 1.

FIG. 3 is a side-sectional view of the wire guide of FIGS. 1-2 in a relaxed state.

FIG. 4 is a side-sectional view of the wire guide of FIGS. 1-2 in a stiffened state.

DETAILED DESCRIPTION OF THE PREFERRED EMBODIMENTS

Figure 5:
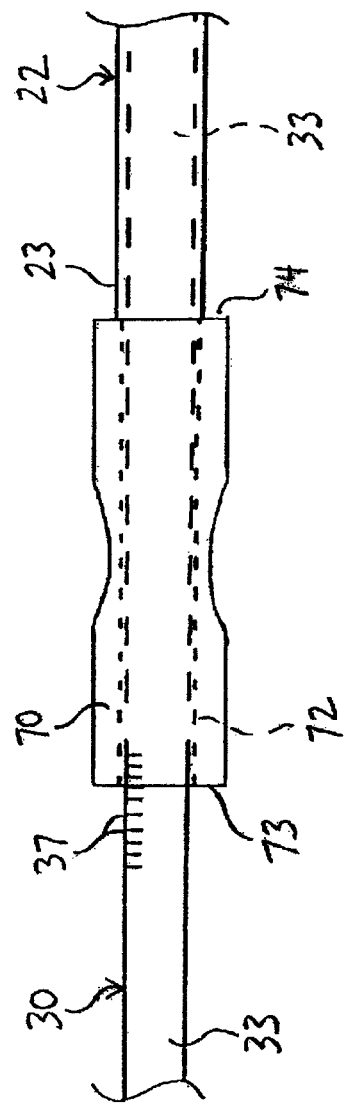
FIG. 5 is a side view of an exemplary activation mechanism that may be used in conjunction with the wire guide of FIGS. 1-4.

In the present application, the term "proximal" refers to a direction that is generally towards a physician during a medical procedure, while the term "distal" refers to a direction that is generally towards a target site within a patient's anatomy during a medical procedure.

Referring now to FIGS. 1-4, a first embodiment of a variable stiffness wire guide is shown. In FIG. 1, the wire guide 20 generally comprises an outer core member 22, an inner core member 30, and a coiled member 40. The outer core member 22 comprises proximal and distal ends 23 and 24, respectively, and a lumen extending between the proximal and distal ends. The proximal end 23 may be coupled to an activation mechanism 70, while the distal end 24 may be attached to the coiled member 40, as set forth in greater detail below.

The inner core member 30 has an outer diameter that is smaller than an inner diameter of the outer core member 22, allowing the inner core member 30 to be disposed within the lumen of the outer core member 22 along a substantial portion of the length of the outer core member 22, as described below. Therefore, the outer and inner core members 22 and 30 are generally coaxially disposed and dimensioned for longitudinal movement with respect to one another.

The coiled member 40 also has an inner diameter that is larger than the outer diameter of the inner core member 30, thereby allowing the inner core member 30 to be disposed within the coiled member 40, as generally shown in FIGS. 2-4 and explained in further detail below. Further, the coiled member 40 may have an outer diameter that is substantially flush with an exterior surface of the outer core member 22, as depicted in FIG. 1.

The outer core member 22 may be manufactured using any suitable material, and preferably is formed as a relatively stiff member such as a stainless steel cannula or hypotube. The inner core member 30 may be manufactured using any suitable material, for example, a solid stainless steel mandrel. The coiled member 40 may be manufactured, for example, from a wound spring wire having a round or flat wire configuration.

The coiled member 40 has a proximal end 43 and a distal end 44. The proximal end 43 of the coiled member 40 is attached to the distal end 24 of the outer core member 22, as depicted in FIG. 1 and FIGS. 3-4. The coiled member 40 may be attached to the outer core member 22 using any suitable technique, for example, soldering, welding or using a biocompatible glue. It should be noted that the inner core member 30 extends distal to the distal end 24 of the outer core member 22, and is not affixed to the proximal end 43 of the coiled member 40, as shown in FIGS. 3-4.

The inner core member 30 is attached to the coiled member 40 at an attachment region 53, which is disposed between the proximal and distal ends 43 and 44 of the coiled member 40, as shown in FIGS. 1-4. The attachment region 53 of the coiled member 40 may comprise a solder, weld, biocompatible glue or other suitable means for affixing the inner core member 30 to the coiled member 40. The inner core member 30 preferably extends distal to the attachment region 53. The distal end 58 of the inner core member 30 may be attached to the atraumatic tip 59, which may comprise a rounded solder 59, as depicted in FIGS. 2-4.

The attachment region 53 therefore divides the coiled member 40 into two sections. The first section, a variable stiffness region v, spans a region between the proximal end 43 and the attachment region 53. The second section, a fixed stiffness region f, spans a region between the attachment region 53 and the atraumatic tip 59, as shown in FIG. 1. As will be explained in greater detail below, the coiled member 40 may be selectively stiffened along the variable stiffness region v, as needed, to vary the flexibility along this region of the wire guide.

In one embodiment, the inner core member 30 may comprise a tapered region 35 and a reduced diameter distal region 34, as shown in FIGS. 2-4. While the tapered region 35 is depicted as starting to taper near the attachment region 53, the tapered region 35 may be positioned at a location further proximal or distal to the attachment region 53. For example, the tapered region 35 may be disposed in the vicinity of the proximal end 43 of the coiled member 40, thereby allowing the reduced diameter distal region 34 to span a greater length.

Optionally, the distal end 44 of the coiled member 40 also may form a taper that reduces the outer diameter of the coiled member towards the atraumatic tip 59. In such an embodiment, the taper of the coiled member 40 may generally follow the tapered region 35 of the inner core member 30, thereby providing a smaller profile along the distal region of the wire guide 20.

In one embodiment, the wire guide 20 may further comprise a safety wire 56, which may be disposed between the attachment region 53 and the atraumatic tip 59. The safety wire 56 may comprise a relatively thin wire, which may be employed as a precaution against leaving a broken wire guide tip in the vascular system of a patient. The safety wire 56 also may reduce the likelihood of kinking in the vicinity of the distal end 44 of the coiled member 40.

The safety wire 56 is disposed within the inner confines of the coiled member 40. The safety wire 56 comprises a proximal end that may be affixed to the attachment region 53, and further comprises a distal end that may be affixed to the atraumatic tip 59, as depicted in FIGS. 2-4. In particular, the distal end of the safety wire 56 may be fused with the solder 59, as shown in FIG. 2.

In order to provide an additional degree of rigidity to the fixed stiffness region f, the safety wire 56 may be disposed adjacent to the reduced diameter distal region 34 of the inner core member 30, as shown in FIG. 2. In this embodiment, the safety wire 56 preferably is configured such that the fixed stiffness region f retains a sufficiently high degree of flexibility to allow the wire guide to navigate tortuous vasculature.

As depicted in FIG. 1, the coiled portion 40 spans only a portion of the overall length of the wire guide 20. For example, the coiled portion 40 may span approximately 5-25% of the total length of the wire guide 20. Depending on the type of wire guide 20, this may be about 4-50 cm of the overall length of the wire guide. Moreover, the distance between the distal end 44 of the coiled member 40 and the attachment region 53, i.e., the length of the fixed stiffness region f, may range from about 1 cm to about 20 cm. The distance between the proximal end 43 and the attachment region 53 in a relaxed state of the wire guide 20, i.e., the length of the variable stiffness region v, may range from about 2 cm to about 30 cm. However, the fixed stiffness region f may have the same length, or a greater length than the variable stiffness region v. Such dimensions are provided for reference purposes only and are not intended to be limiting.

Referring now to FIGS. 3-4, the general use of the wire guide 20 is described. In FIG. 3, the wire guide 20 is shown in a relaxed state, whereby the outer core member 22 is positioned a first distance relative to the attachment region 53 corresponding to the uncompressed length of the variable stiffness region v. Preferably, in this relaxed state, few external forces, if any, are acting upon the coiled member 40, thereby allowing the coiled member 40 to exhibit flexibility along its entire length between the proximal end 43 and the distal end 44. This state may be well-suited for introduction of the distal region of the wire guide 20 through a patient's tortuous vasculature, as both the variable stiffness region v and the fixed stiffness region f exhibit flexible characteristics.

Referring to FIG. 4, the outer core member 22 has been advanced distally with respect to the inner core member 30, for example, using an activation mechanism 70, as described in FIG. 5 below. More specifically, the outer core member 22 is advanced distally, while the inner core member 30 is held longitudinally steady. Therefore, the proximal end 43 of the coiled member 40 moves closer to the attachment region 53, thereby reducing the length of the variable stiffness region v and causing the coiled member 40 to compress along the variable stiffness region v, as generally depicted in FIG. 4. In this state, the coiled member 40 may exhibit stiffer characteristics along the variable stiffness region v, relative to the relaxed state depicted in FIG. 3. It should be noted that the flexibility of the coiled member 40 along the fixed stiffness region f remains substantially the same, as the length of the coiled member 40 between the attachment region 53 and the atraumatic tip 59 is not changed.

The relatively stiff state depicted in FIG. 4 may be well-suited for introduction of medical components, such as a catheter, over the wire guide 20. Specifically, since the outer core member 22 is always relatively stiff, and since the variable stiffness region v may also be relatively stiff in the state depicted in FIG. 4, a substantial portion of the length of the wire guide 20 thus may be relatively stiff, with the exception of the fixed stiffness region f. The enhanced stiffness provided by the variable stiffness region v may reduce the likelihood that the wire guide 20 will kink along a substantial portion of its length during the advancement of a catheter or other medical devices.

Therefore, the wire guide 20 of FIGS. 1-4 generally includes a relatively stiff proximal portion comprising the outer core member 22, a relatively flexible distal portion having a fixed stiffness region f, and a variable stiffness region v, which may vary the flexibility along a part of the relatively flexible distal portion of the wire guide 20. The variable stiffness region v may be provided in the relaxed state of FIG. 3 during insertion of the wire guide 20 to navigate vasculature, and may be transitioned to the relatively stiff state of FIG. 4, for example, during insertion of medical components over the wire guide 20.

Referring now to FIG. 5, an exemplary activation mechanism 70, which may be used to control the variable stiffness region v of the wire guide 20, is described. The activation mechanism 70 has first and second ends 73 and 74, respectively, and may be provided, for example, in the form of a block-shaped handle that may be grasped by a human hand. The proximal end 23 of the outer core member 22 may be affixed to the second end 74 of the activation mechanism 70. Further, the inner core member 30 may be disposed through an inner bore 72 formed through the block-shaped handle of the activation mechanism 70, as shown in FIG. 5.

In order to vary the stiffness of the variable stiffness region v of the wire guide 20, the inner core member 30 is held steady while the activation mechanism 70 is proximally retracted or distally advanced. Specifically, distal advancement of the activation mechanism 70 with respect to the inner core member 30 causes distal advancement of the outer core member 22 to stiffen the variable stiffness region v, as explained with respect to FIG. 4 above. Conversely, proximal retraction of the activation mechanism 70 with respect to the inner core member 30 may relax the variable stiffness region v to provide increased flexibility, as depicted in FIG. 3 above.

The proximal end 33 of the inner core member 30 may include measurement indicia 37 to provide the physician with a measurement of stiffness along the variable stiffness region v since the stiffness along the variable stiffness region v is related to the positioning of the outer core member 22 relative to the inner core member 30. For example, if the first end 73 of the activation mechanism 70 is aligned with a proximal one of the measurement indicia 37, then the coiled member 40 may be relatively flexible along the variable stiffness region v. By contrast, if the first end 73 of the activation mechanism 70 is aligned with a distal one of the measurement indicia 37, then the coiled member 40 may be compressed, i.e., relatively stiff, along the variable stiffness region v.

In one embodiment, the activation mechanism 70 may be selectively rotated in a circumferential direction about the inner core member 30 so as to provide a selective axial adjustment of the outer core member 22 with respect to the inner core member 30. For example, the inner bore 72 may have internal threading that engages with external threading provided along the proximal end 33 of inner core member 30. The threaded engagement may permit incremental axial positioning of the activation mechanism 70 to selectively vary the stiffness along the variable stiffness region v. Alternatively, both the inner bore 72 and an outer surface of the inner core member 30 may be dimensioned so as to provide a frictional fit therebetween, which allows for selective longitudinal advancement of the activation mechanism 70, while reducing the likelihood of inadvertent longitudinal movement of the activation mechanism.

Figure 6:
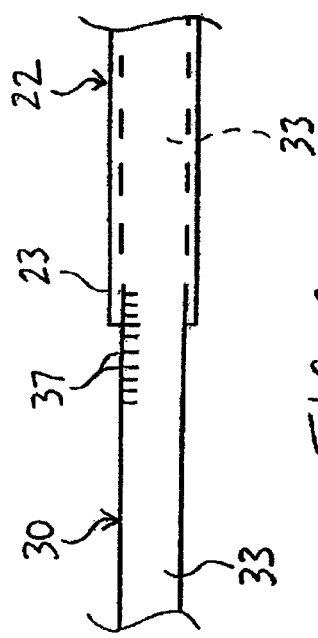
FIG. 6 is a side view of an alternative activation mechanism that may be used in conjunction with the wire guide of FIGS. 1-4.

Referring now to FIG. 6, in an alternative embodiment, the activation mechanism 70 may be omitted and the inner core member 30 may be coupled directly to the outer core member 22. Like the embodiment of FIG. 5 above, the proximal end 23 of the outer core member 22 may comprise internal threading that engages external threading provided along the proximal end 33 of the inner core member 30. Alternatively, the proximal end 23 may employ a reduced-diameter friction fit to allow for selective longitudinal advancement of the outer core member 22 with respect to the inner core member 30, while reducing the likelihood of inadvertent longitudinal movement.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A wire guide suitable for use in a body vessel, the wire guide comprising:
   an outer core member having proximal and distal ends;
   an inner core member having proximal and distal ends, the inner core member being disposed for longitudinal movement with respect to the outer core member; and
   a coiled member having proximal and distal ends, wherein the distal end of the outer core member is attached to the proximal end of the coiled member, and the inner core member is attached to the coiled member at an attachment region between the proximal and distal ends of the coiled member,
   wherein the outer core member is configured to be advanced distally with respect to the inner core member to causes the coiled member to compress along a variable stiffness region spanning a full length between the proximal end of the coiled member and the attachment region, and
   wherein the inner core member is positioned without any intervening member between the inner core member and the coiled member along the full length of the variable stiffness region and the inner core member comprises a uniform diameter along the full length of the variable stiffness region.

2. The wire guide of claim 1 wherein the inner core member extends beyond the attachment region to the distal end of the coiled member.

3. The wire guide of claim 2 wherein the inner core member is tapered between the attachment region and the distal end of the coiled member.

4. The wire guide of claim 1 wherein the inner core member is soldered to the coiled member at the attachment region.

5. The wire guide of claim 1 further comprising a safety wire disposed between the attachment region and the distal end of the coiled member.

6. The wire guide of claim 1 further comprising an activation mechanism for causing selective advancement of the outer core member in proximal and distal directions with respect to the inner core member.

7. The wire guide of claim 6 wherein the activation mechanism comprises a rotatable handle.

8. The wire guide of claim 1 wherein there is a uniform spacing between the inner core member and the coiled member along the entire variable stiffness region.

9. The wire guide of claim 1 wherein an inner surface of the coiled member is supported by the inner core member along the entire variable stiffness region.

10. A method for varying the stiffness of at least a portion of a wire guide, the method comprising:
    providing an outer core member having proximal and distal ends and an inner core member having proximal and distal ends, the inner core member being disposed for longitudinal movement with respect to the outer core member; and
    providing a coiled member having proximal and distal ends, wherein the distal end of the outer core member is attached to the proximal end of the coiled member, and the inner core member is attached to the coiled member at an attachment region between the proximal and distal ends of the coiled member,
    longitudinally advancing the outer core member with respect to the inner core member to cause the coiled member to compress along a variable stiffness region spanning a full length between the proximal end of the coiled member and the attachment region, thereby varying the stiffness of the coiled member between the proximal end of the coiled member and the attachment region, and
    wherein the inner core member is positioned without any intervening member between the inner core member and the coiled member along the full length of the variable stiffness region.

11. The method of claim 10 further comprising soldering the inner core member to the coiled member at the attachment region.

12. The method of claim 10 further comprising providing a safety wire disposed between the attachment region and the distal end of the coiled member.

13. The method of claim 10 further comprising using an activation mechanism to cause a selective advancement of the outer core member in proximal and distal directions with respect to the inner core member.

14. The method of claim 13 wherein the activation mechanism comprises a rotatable handle, the method further comprising rotating the rotatable handle to cause selective movement of the outer core member with respect to the inner core member.

15. The method of claim 10 wherein the inner core member extends beyond the attachment region to the distal end of the coiled member.

16. A wire guide suitable for use in a body vessel, the wire guide comprising:
    an outer core member having proximal and distal ends;
    an inner core member, the inner core member being disposed for longitudinal movement with respect to the outer core member; and
    a coiled member connected to the outer core member and the inner core member, wherein the coiled member comprises proximal and distal ends, wherein the distal end of the outer core member is attached to the proximal end of the coiled member,
    the coiled member having a variable stiffness region and a fixed stiffness region, the variable stiffness region being formed at a location proximal to the fixed stiffness region,
    wherein the inner core member is positioned without any intervening member between the inner core member and the coiled member along a full length of the variable stiffness region, and
    wherein of the outer core member is configured to be moved with respect to the inner core member to vary the stiffness of the coiled member along the variable stiffness region.

17. The wire guide of claim 16, wherein the inner core member is attached to the coiled member at an attachment region between the proximal and distal ends of the coiled member.

18. The wire guide of claim 17 wherein the inner core member extends beyond the attachment region to the distal end of the coiled member.

19. The wire guide of claim 17 wherein the inner core member is tapered between the attachment region and the distal end of the coiled member.

20. The wire guide of claim 17 wherein the inner core member is soldered to the coiled member at the attachment region.

21. The wire guide of claim 17 further comprising a safety wire disposed between the attachment region and the distal end of the coiled member.

22. The wire guide of claim 16 further comprising an activation mechanism for causing selective advancement of the outer core member in proximal and distal directions with respect to the inner core member.

23. The wire guide of claim 22 wherein the activation mechanism comprises measurement indicia for providing a measurement of stiffness along the variable stiffness region.

24. The wire guide of claim 23 wherein the measurement indicia provide a measurement of stiffness along the variable stiffness region by indicating the positioning of the outer core member relative to the inner core member.

25. The wire guide of claim 16 wherein the outer core member is adapted to be incrementally axially positioned with respect to the inner core member to permit incremental stiffness variations along the variable stiffness region.

* * * * *